United States Patent
Fecher et al.

(10) Patent No.: US 8,685,294 B2
(45) Date of Patent: Apr. 1, 2014

(54) METHOD OF PRODUCING A DENTAL CERAMIC STRUCTURE

(75) Inventors: Stefan Fecher, Johannesberg (DE); Lothar Völkl, Goldbach (DE)

(73) Assignee: Degudent GmbH, Hanau (DE)

( * ) Notice: Subject to any disclaimer, the term of this patent is extended or adjusted under 35 U.S.C. 154(b) by 1486 days.

(21) Appl. No.: 11/013,795

(22) Filed: Dec. 17, 2004

(65) Prior Publication Data
US 2005/0146064 A1    Jul. 7, 2005

(30) Foreign Application Priority Data
Dec. 17, 2003    (EP) ..................................... 03028902

(51) Int. Cl.
*A61C 13/00*    (2006.01)
(52) U.S. Cl.
USPC ............................................. 264/19; 264/14
(58) Field of Classification Search
USPC .................................................... 264/19, 14
See application file for complete search history.

(56) References Cited

U.S. PATENT DOCUMENTS

| 5,092,022 A |   | 3/1992 | Duret |
|---|---|---|---|
| 5,224,049 A | * | 6/1993 | Mushabac ..................... 700/163 |
| 5,347,454 A |   | 9/1994 | Mushabac |
| 5,382,164 A | * | 1/1995 | Stern ............................ 433/223 |
| 6,691,764 B2 | * | 2/2004 | Embert et al. ................. 164/4.1 |
| 2002/0125619 A1 | * | 9/2002 | Bodenmiller et al. ........ 264/678 |

FOREIGN PATENT DOCUMENTS

| DE | 19 630412 | 1/1998 |
|---|---|---|
| DE | 10 136584 | 3/2002 |
| JP | 09 019443 | 1/1989 |
| WO | 94 21214 | 9/1994 |
| WO | 03 017864 | 3/2003 |

OTHER PUBLICATIONS

"AutoCAD" Feb. 12, 2010 <http://en.wikipedia.org/wiki/AutoCAD>.*

\* cited by examiner

*Primary Examiner* — Galen Hauth
(74) *Attorney, Agent, or Firm* — Ladas & Parry LLP

(57) ABSTRACT

Method of producing a dental ceramic structure by digitizing a model or partial model of the prosthesis to be produced and generating a CAD data set, cutting each section of the muffle based on the CAD data set to form the cavity, pressing the ceramic into the cavity by way of at least one sprue, removing the hardened ceramic from the cavity with the sprue or flash and removing the sprue or flash based on the CAD data set.

5 Claims, 3 Drawing Sheets

METHOD OF PRODUCING A DENTAL CERAMIC STRUCTURE

BACKGROUND OF THE INVENTION

The invention relates to a method of producing a dental ceramic structure, in particular, for pressing against, over or around a supporting structure made of metal or ceramic using a muffle having two sections which define a cavity corresponding to the negative form of the structure, flowable material being supplied into the cavity via at least one sprue.

A corresponding method is known, for example, from DE-A 196 30 412 for producing a ceramic dental structure. With this method, the steps are as follows: an impression of the mouth situation is taken with inserted ceramic root pin, a mold is made from the impression whereby the pin protrudes from the mold, a reconstruction is made from an annealable material, a sprue attached, a pin and waxed parts are embedded in a muffle with a hardenable embedding substance, the wax is removed by heating and finally the ceramic pressed in.

The quality of the dental ceramic structure thereby depends, on the one hand, on the skill of the dental technician who undertakes the molding of the reconstruction and, on the other hand, on the formation of the cavity with the embedded substance which surrounds the molding.

A corresponding method can also be found in DE-A 101 36 584 A1.

A method of producing dental prostheses is known from U.S. Pat. No. 5,092,022. In this case, according to the embodiment of FIG. 27, a molded part is formed by cutting, from a block consisting, for example, of metal, on the basis of stored data which corresponds to the outer geometry of a dental ceramic structure to be produced. The cavity thus formed is defined by a mold part accommodating a metal structure A sprue into which the liquid material, e.g. synthetic resin, is introduced extends between the mold parts.

SUMMARY OF THE INVENTION

The object of the present invention is to further develop a method of the aforementioned type in such a manner that highly precise dental ceramic structures are provided in which defects can be largely avoided due to manual intervention.

To solve the object, the invention provides the following method steps:
a) digitizing a model or partial model of the dental prosthesis to be produced and generating a CAD data set of the dental prosthesis to be produced,
b) cutting each section of the muffle based on the CAD data set to form the cavity,
c) pressing the ceramic, as the material to be supplied, into the cavity byway of the at least one sprue,
d) after hardening the ceramic, removing the structure from the cavity with the sprue or flash thereof extending from the structure, and
e) removing the sprue or flash on the basis of the CAD data set of the structure to be produced.

In particular, the method in which the dental ceramic structure comprises a supporting structure is distinguished in that the structure is placed in the cavity after it has been formed (procedural step b), after which the ceramic is pressed into the cavity over the structure and procedural steps d) and e) are ultimately carried out.

In particular, the mold cavity is formed from a hardened embedding substance.

According to the invention, the supporting structures are molded or pressed over for e.g. crowns or bridges in an automated production based on CAD data. For this purpose, the negative mold of the structure to be produced is, for example, worked out by milling in a suitable blank such as an embedding substance. The volume of the ceramic material to be pressed in is then produced from the geometry obtained on the basis of the CAD data and thus its volume less the volume of a prefabricated and used structure. The molding ceramic is then pressed onto or around the structure. The dental structure, such as a crown or bridge, can then be removed from the mold in order to then be basically used immediately. If necessary, a minimal refinishing is required.

BRIEF DESCRIPTION OF THE DRAWINGS

Further details, advantages and features of the invention can be found not only in the claims, the features found therein—alone and/or in combination—but also in the following description of a preferred embodiment found in the drawings, in which:

DESCRIPTION OF THE PREFERRED EMBODIMENTS

Figure 1:
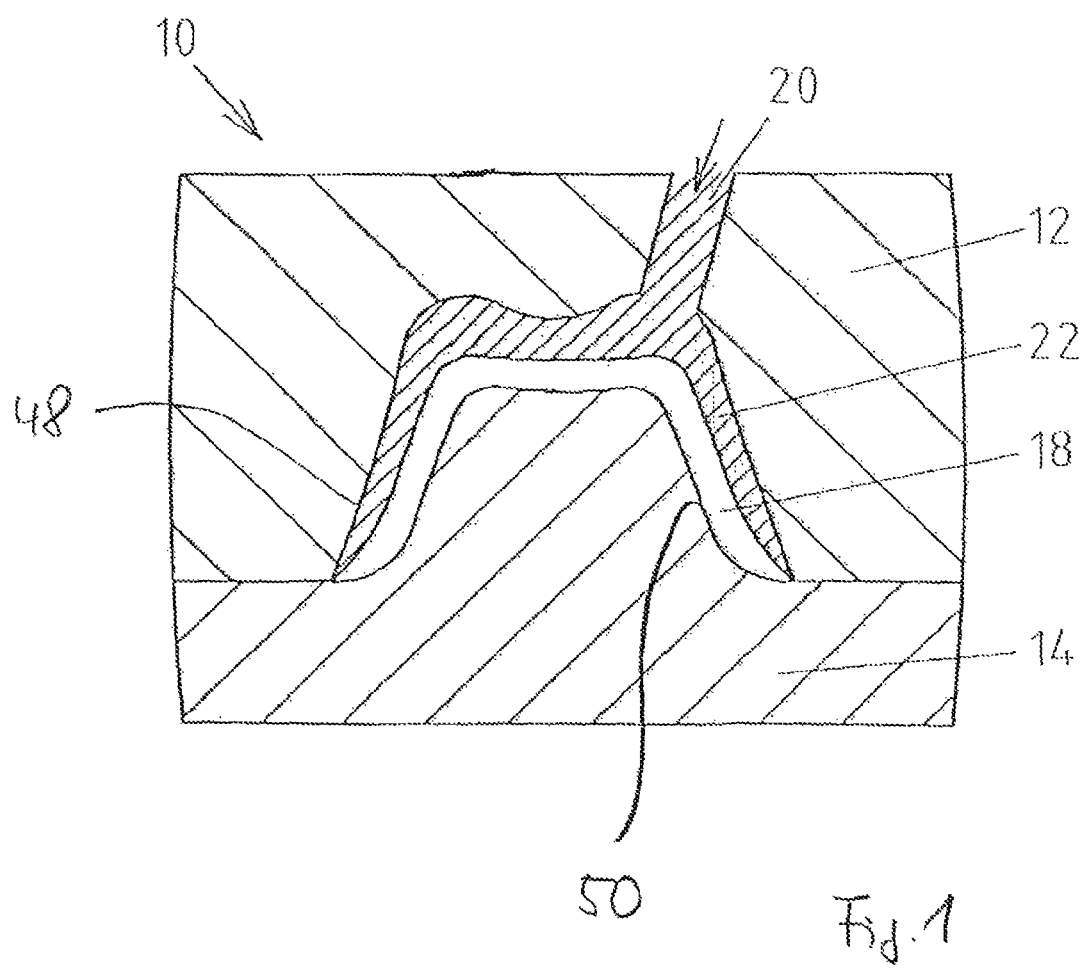
FIG. 1 shows a basic representation of a muffle with a dental ceramic structure formed in it.

In FIG. 1, a muffle 10 is shown which consists of sections 12, 14 that have been fitted together. The sections 12, 14 define a cavity 22 in which a dental ceramic structure is to be produced by pressing around a supporting structure 18.

The internal geometry of the cavity 22 is produced on the basis of CAD data of the dental ceramic structure to be produced from blanks by machining, e.g. by cutting such as milling, which forms the sections 12, 14.

The volume of the cavity 22 not filled by the structure 18 is calculated on the basis of the available CAD data in order to then inject molding ceramic (hatched area 22) via a sprue 20. After hardening, the sections 12, 14 are separated from one another, the dental ceramic structure removed and then the flash of the sprue 20 is removed. This takes place automatically since the data available for this are used.

To generate the CAD data, an impression can be made of the tooth stump or stumps from a dental preparation, the impression forming a negative mold of the situation in the patient's mouth. The surface of the tooth stump or stumps, approximate surfaces of the adjacent teeth and counter bite are thereby determined. A positive mold, preferably consisting of plaster or plastic, is obtained from this mold. The dental ceramic structure can then be calculated taking into consideration the data obtained from the positive mold by scanning in order to machine, e.g. cut, the sections 12, 14 of the muffle 10 on the basis of the CAD data then available, in order to form the cavity 22 as a whole.

Figure 2:
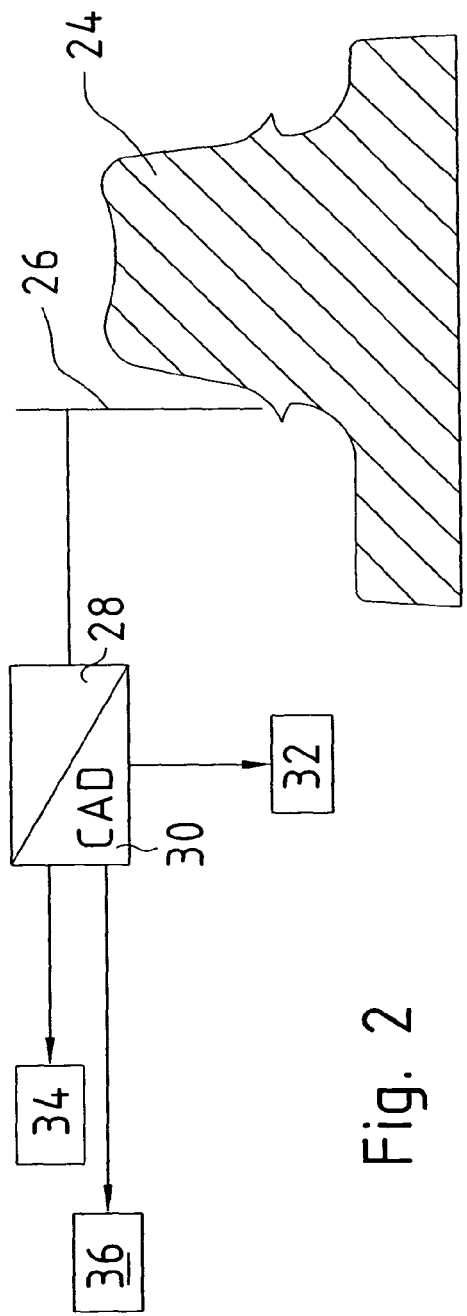
FIGS. 2-5 show basic representations to illustrate the method of producing the dental ceramic structure.
Figure 3:
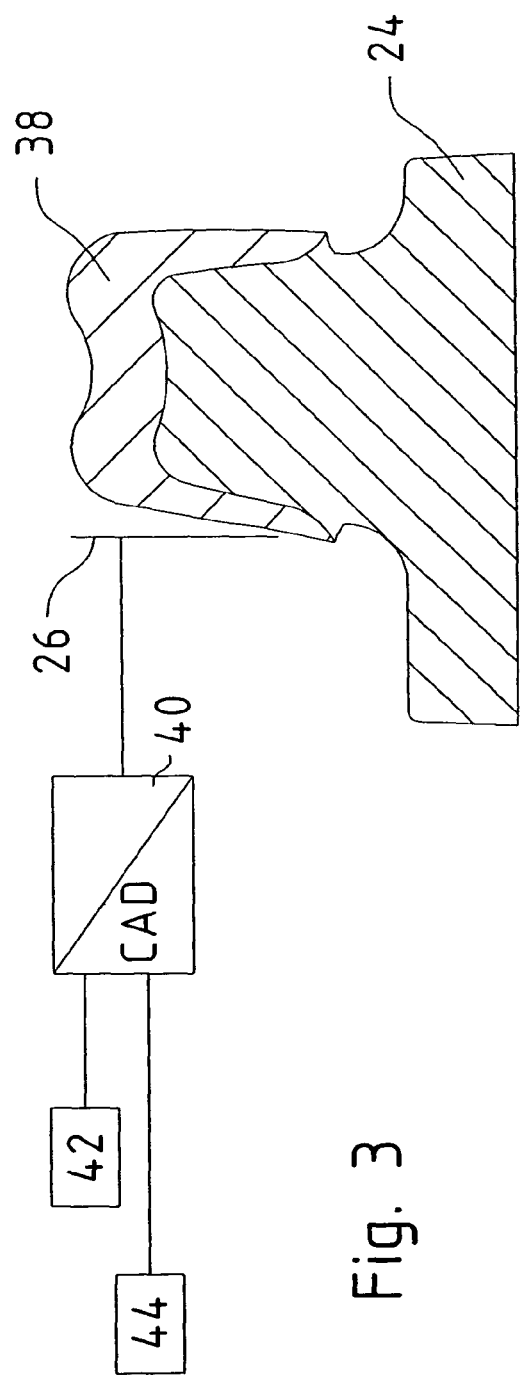
Figure 4:
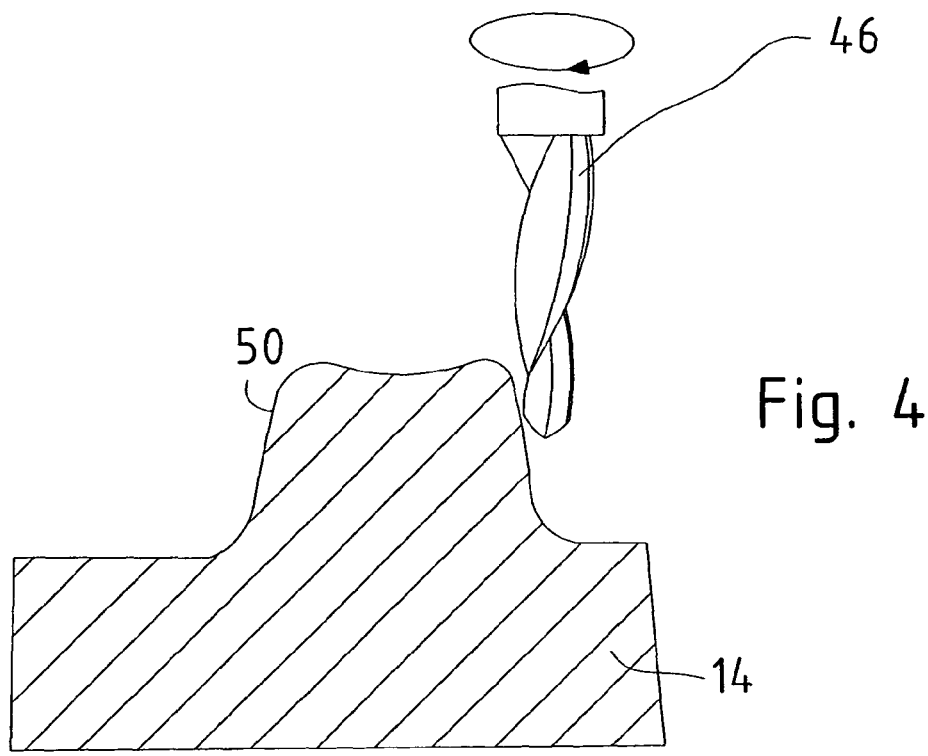
Figure 5:
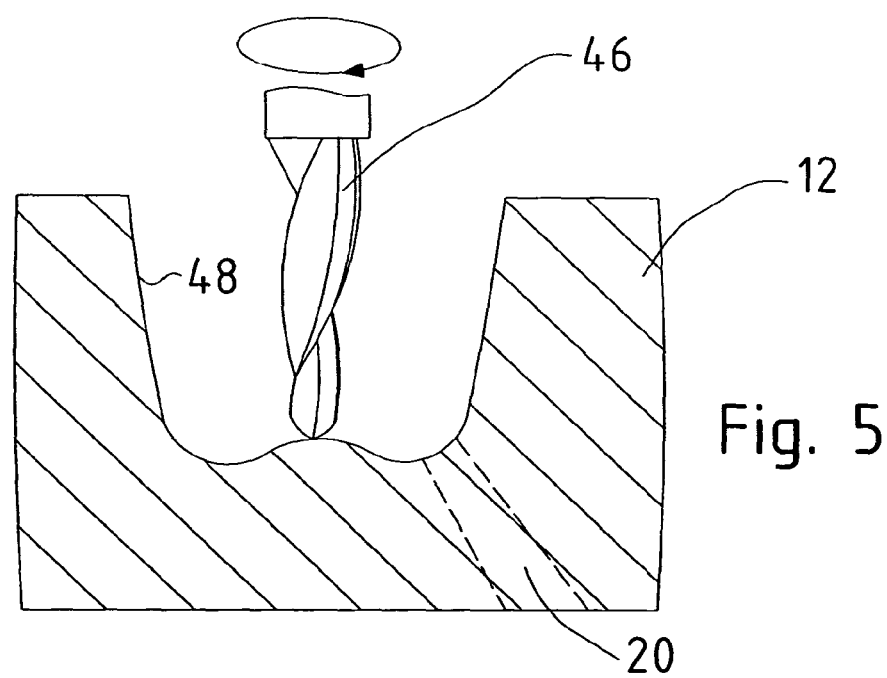

The corresponding procedural steps follow from a synopsis of FIGS. 2, 4 and 5. Thus, a positive mold of one or more tooth stumps is shown in principle in FIG. 2 which are to be provided with a dental ceramic structure. The positive mold 24, i.e. the area which is to be e.g. crowned, is scanned, for example, by means of a mechanical scanner 26 in contact with it or by means of a laser in a non-contact manner, in order to then supply the corresponding data to a computer 28. The corresponding data are then processed by means of a CAD program 30 to obtain data 32, on the basis of which the section 14 of the muffle is produced mechanically, e.g. by cutting.

Furthermore, data 34 are produced which correspond to the entire dental ceramic structure with the result that the section 12, with respect to the area which defines the cavity 18, can be produced from the data 32, 34. Furthermore, data 36 can be generated which correspond to a structure to be produced. If the corresponding data are available, they must first be input into the computer 28 to obtain adapted data 34 for the dental ceramic structure without a supporting structure.

Alternatively, a molding for the dental ceramic structure can be prepared on the positive mold, a corresponding supporting structure for a crown or a bridge being situated on the tooth stump or stumps. The finished mold is then scanned in order to be able to work out the cavity 22 in the muffle 10 on the basis of this data. Of course, it is thereby necessary that the data of the supporting structure used be taken into consideration.

As in the previous explanations, e.g. a cap 38 can be formed on the positive mold 24, the cap corresponding to the dental ceramic structure. The cap 38 is then scanned by non-contact or contact in order to supply the corresponding data to a computer 40 by means of which and by means of a suitable CAD program data 42 for forming the section 12 in its area defining the cavity and, in the event data of the structure is not already available, data for the structure 44 are then generated.

Based on the data 32 or 34, 42, the lower section 14 or the upper section 12 is then formed in a CNC-controlled manner, for example, by means of a milling tool 46. The surfaces 48, 50 thus produced define the cavity 18. Furthermore, it can be seen that the sprue 20 should not be formed in section 12 (hatched illustration), namely also based on the existing digitalized data.

The muffle is then inserted into a known muffle system in order to press flowable ceramic into the cavity 22 or the cavity not filled by the supporting structure 18 via the sprues 20. Press dies are used in the conventional manner for the molding. However, in this respect, reference is made to sufficiently known techniques and constructions. For example, reference is made to DE-U 90 01 740 or DE-A 101 36 584.

Since, as mentioned, the data of the cavity and thus the outer geometry of the finished dental ceramic structure are available, it is easy to automatically remove the flash of the sprue 20.

The invention is claimed is:

1. A method of producing a dental ceramic structure using a muffle having two sections which define a cavity corresponding to a negative shape of the structure, comprising the steps of:
    obtaining a positive mold of a section of a mouth of a patient that is to be provided with a dental ceramic structure;
    scanning the positive mold to obtain data corresponding to the structure, and storing the data in a computer;
    processing the data in the computer using CAD software to obtain CAD data;
    milling or processing using machining based on the CAD data to form first and second sections of the muffle to define a mold cavity corresponding to a negative shape of the structure;
    assembling the first and second sections of the muffle to create the mold cavity, and using the CAD data to calculate volume of the mold cavity;
    placing a support structure inside said mold cavity;
    injecting into the mold cavity the calculated volume of ceramic material through at least one sprue;
    hardening the ceramic material to form the dental ceramic structure that includes the support structure, and subsequently removing the dental ceramic structure and support structure from the mold cavity; and
    removing sprue or flash material from the dental ceramic structure that includes the support structure, using machining based on the CAD data.

2. The method according to claim 1, wherein the dental ceramic structure comprises a supporting structure, and after forming the mold cavity, the structure is placed in the mold cavity and the ceramic is pressed into the mold cavity over the structure.

3. The method according to claim 1, wherein the mold cavity is surrounded by a hardened embedding material.

4. The method according to claim 1, wherein the sections of the muffle defining the mold cavity are cut by milling or grinding.

5. The method according to claim 1, wherein a plurality of sprues opening into the mold cavity are formed for injection of the ceramic.

\* \* \* \* \*

UNITED STATES PATENT AND TRADEMARK OFFICE
CERTIFICATE OF CORRECTION

| | | |
|---|---|---|
| PATENT NO. | : 8,685,294 B2 | Page 1 of 1 |
| APPLICATION NO. | : 11/013795 | |
| DATED | : April 1, 2014 | |
| INVENTOR(S) | : Fecher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1417 days.

Signed and Sealed this
Eighth Day of September, 2015

Michelle K. Lee
*Director of the United States Patent and Trademark Office*